US00PP21721P3

(12) United States Plant Patent
Patel

(10) Patent No.: US PP21,721 P3
(45) Date of Patent: Feb. 22, 2011

(54) BLUEBERRY VARIETY NAMED 'F126'

(50) Latin Name: ***Vaccinium corymbosum* hybrid**
Varietal Denomination: F126

(75) Inventor: Narandra Patel, Hamilton (NZ)

(73) Assignee: The New Zealand Institute for Plant and Food Research Limited, Auckland (NZ)

( * ) Notice: Subject to any disclaimer, the term of this patent is extended or adjusted under 35 U.S.C. 154(b) by 0 days.

(21) Appl. No.: 12/590,267

(22) Filed: Nov. 5, 2009

(65) Prior Publication Data

US 2010/0115676 P1 May 6, 2010

Related U.S. Application Data

(60) Provisional application No. 61/198,522, filed on Nov. 6, 2008.

(51) Int. Cl.
*A01H 5/00* (2006.01)

(52) U.S. Cl. ..... Plt./157

(58) Field of Classification Search ..... Plt./157
See application file for complete search history.

*Primary Examiner*—Annette H Para
(74) *Attorney, Agent, or Firm*—Greenlee Sullivan PC

(57) ABSTRACT

A new and distinct Southern Highbush blueberry variety is described. The variety results from selection among a population of seedlings derived from crossing the blueberry variety known as 'Reka' (U.S. Plant Pat. No. 6,700) and the blueberry variety known as 'Island Blue' (not patented). The fruit of this new variety is small, round, with an attractive appearance characterized by good bloom; fruit has an outstanding quality, sweet, and with a low acidity content. Plant is upright with good vigor, heavy crop early in the summer and a potential second crop late in the summer.

7 Drawing Sheets

Genus and species of plant named: *Vaccinium corymbosum* hybrid.

Variety denomination: F126.

BACKGROUND OF THE INVENTION

This new Southern Highbush variety was selected from a population of seedlings derived from crossing the blueberry varieties known as 'Reka' (U.S. Plant Pat. No. 6,700) and the blueberry variety known as 'Island Blue' (not patented). The cross was made in 1990 and the new variety was selected in 1998 from among plants located on land at Ruakura, Hamilton, New Zealand, and was assigned the breeder code, F126. The variety was initially named 'Kristel Blue' but the name has been abandoned.

SUMMARY OF THE INVENTION

The fruit of this new variety is small, round, with an attractive appearance characterised by good bloom; fruit has an outstanding quality, sweet, and with a low acidity content. Plant is upright with good vigour, heavy crop early in the summer and a potential second crop late in the summer.

The new variety is characterised as follows:

Maturity period: The new variety produces two crops under the environmental conditions prevailing at Ruakura, Hamilton, New Zealand. The main crop is early season, from the end of November to mid December, about a week earlier than 'Reka' and about 10 days later than the parent 'Island Blue' which is considered as very early maturing under New Zealand conditions. The second crop is of less account and generally occurs late in the summer, around February at Ruakura, Hamilton, New Zealand.

Plant form and vigour: The plant is upright with good vigour, similar to 'Reka'.

Yield: Heavy crop early in the summer, superior to 'Reka' and 'Island Blue'.

Berry size and shape: Small and round fruit, smaller than the fruit of 'Reka' and 'Island Blue'.

Color: Medium to light blue.

Fruit bloom: Strong intensity, attractive.

Pedicel scar: Small to medium dry scar similar to 'Reka' and 'O'Neal'.

Plant health: The plant has shown symptoms of the early stage of rust infection (*Pucciniastrum vaccinii*) with little subsequent sporulation.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

FIG. 1 shows a young plant (3 years old) of F126 during flowering.

FIGS. 2A and 2B show typical adult upright plants of F126 planted in the field. FIG. 2A was taken at the end of the summer (April 2009). FIG. 2B shows the same plant in the following spring (September 2009).

DETAILED DESCRIPTION

Figure 1:
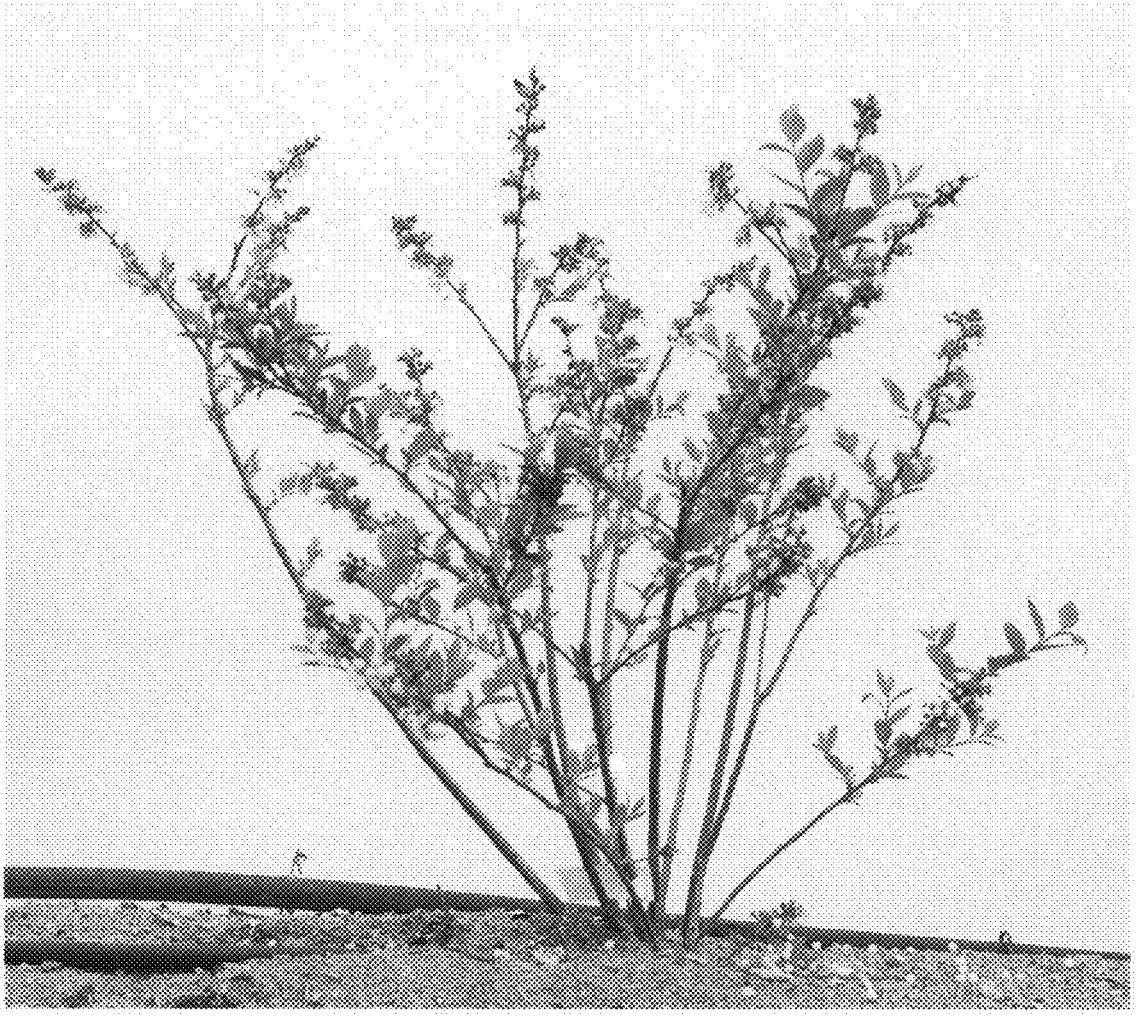
Figure 2A:
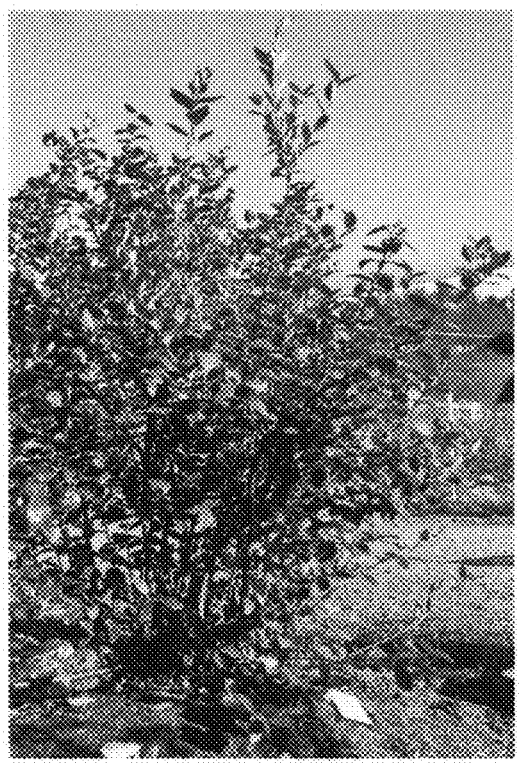
Figure 2B:
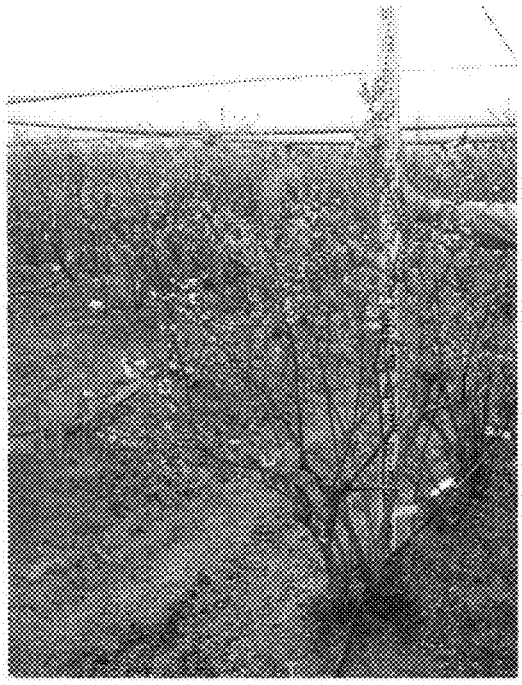
Figure 3:
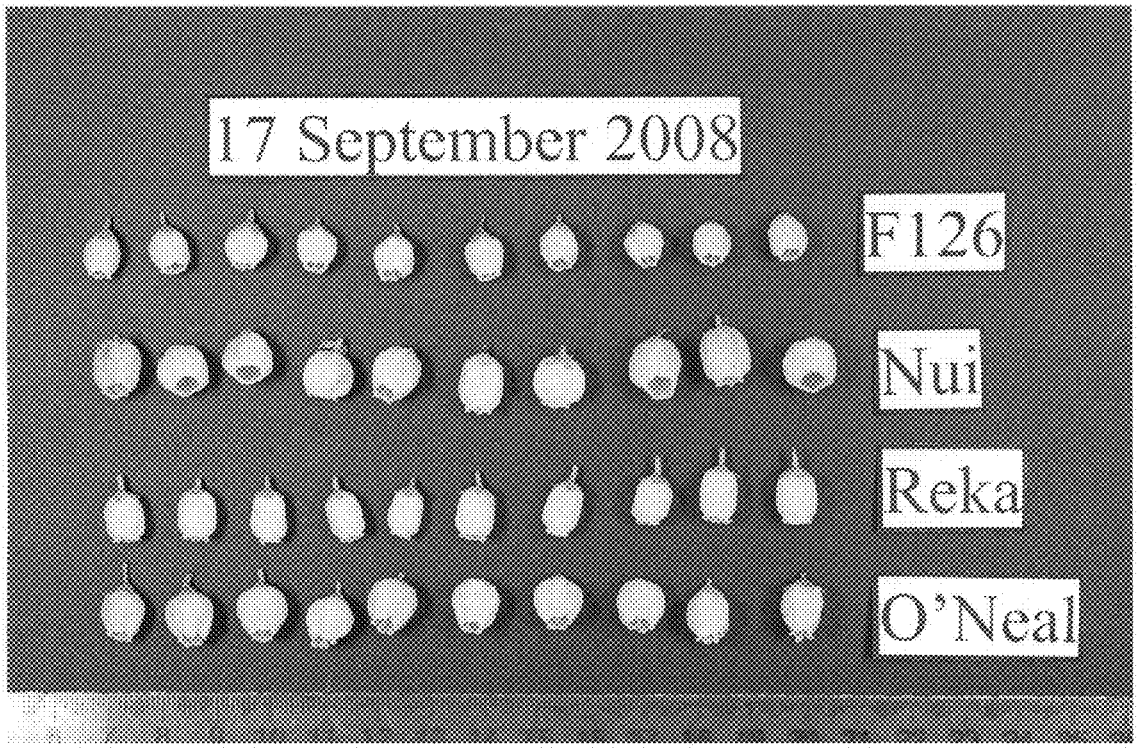
FIG. 3 shows the characteristic flowers of F126 compared to flowers of commercial varieties.
Figure 4:
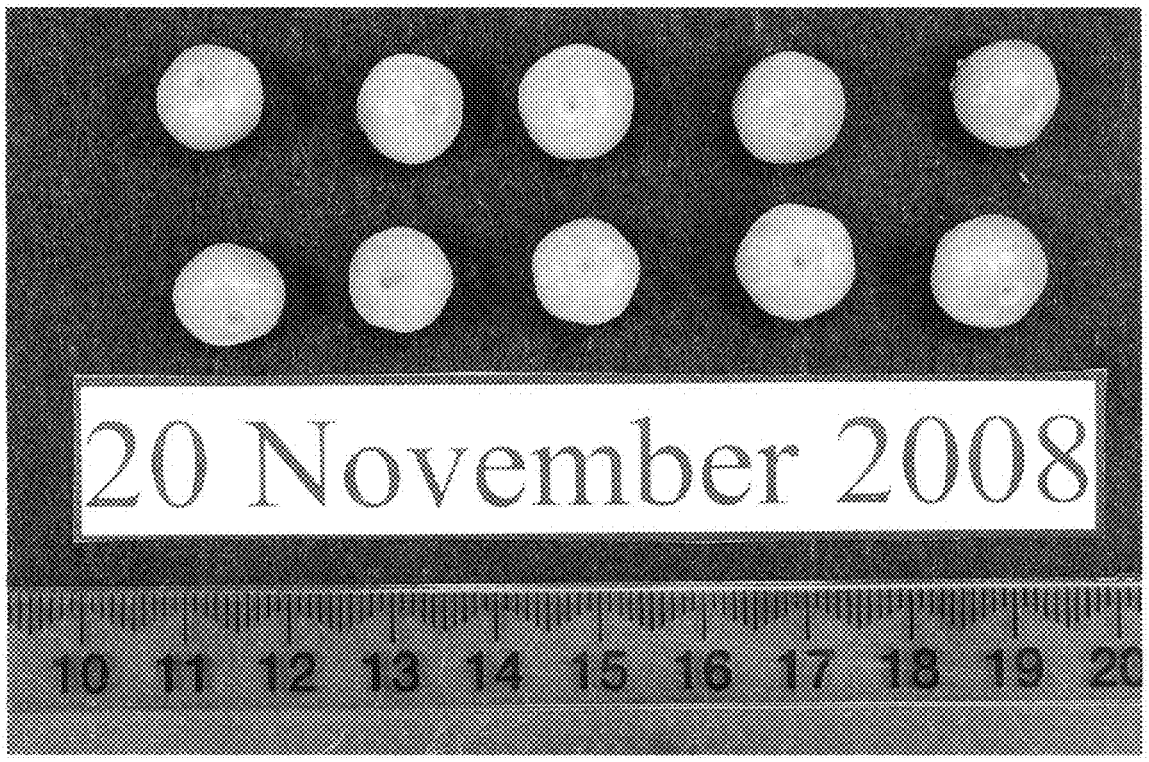
FIG. 4 shows the typical green fruit of F126.
Figure 5:
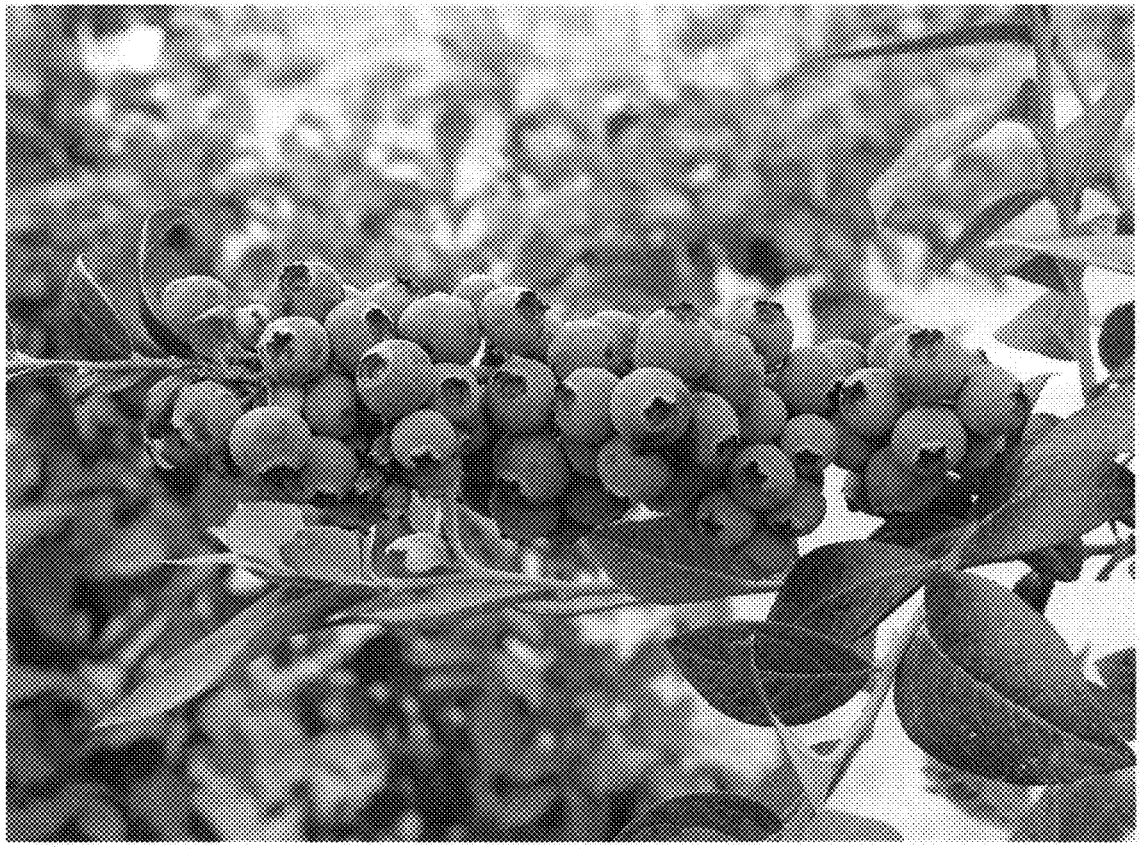
FIG. 5 shows a typical fruit bunch of adult plant of F126 during the main first crop.
Figure 6:
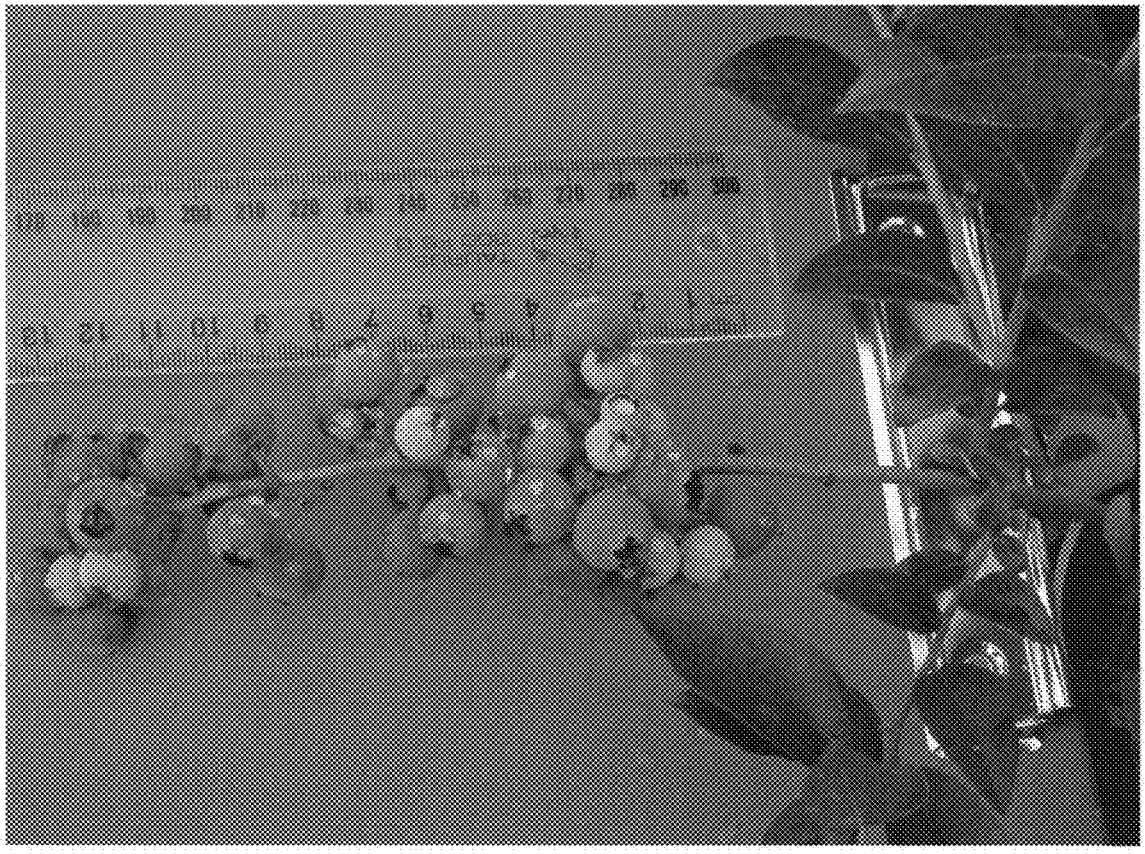
FIG. 6 shows the small fruit size of F126 during the first main crop.
Figure 7:
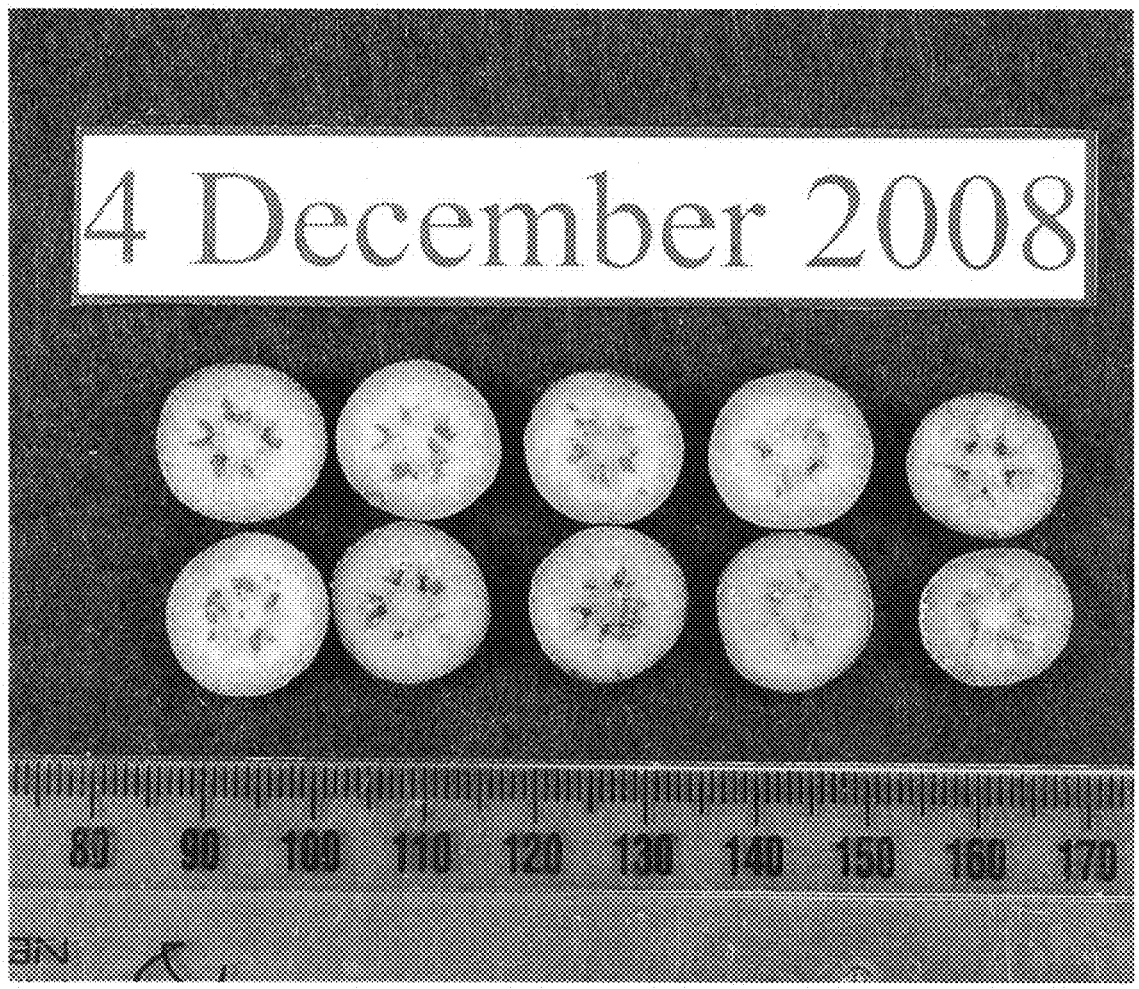
FIG. 7 shows the fruit section of F126.

The observations, unless otherwise specified, were made in the 2008 and 2009 seasons on nine year old plants propagated and grown at Ruakura, Hamilton, New Zealand and additional information was collected from young plants (3-5 years old). All dimensions in millimeters, weights in grams (unless otherwise stated). Color terminology is in accordance with The Royal Horticultural Society Colour Charts 2001 edition.

Plant and Foliage

This tetraploid plant is generally upright in habit, with good vigour, similar to 'Reka'. The mature leaf is ovate in shape and typically averages 51 mm in length and approximately 34 mm in width, smaller than the leaf size of plants of the varieties 'Reka' (U.S. Plant Pat. No. 6,700) (63 mm in length and 36 mm in width), 'Duke' (70 mm in length, 42 mm in width), and 'Nui' (80 mm in length, 50 mm in width). Generally the leaf margin has no serration, medium glossiness on the upper surface, and no glaucescence on the upper surface. Typically the petiole length averages 3 mm.

The color of the leaf is near Green 139A, similar to 'Reka' and different from those of the variety 'Nui' (near green 146A). Leaf vein color is near Yellow-Green 146A, different compared with those of the variety 'Nui' (near Yellow-Green 152C).

The color of mature dormant wood is near Greyed-Purple 185C on the top side of the cane and Yellow-Green 144C on the underside of the same cane, differing from that of the variety 'Nui' near Greyed-Red 181A and B on the top side of the cane and Yellow-Green 146C on the underside of the same cane.

Inflorescence

The average number of flower buds per shoot is 7, with an observed range of 3-13. The estimation of number of buds per shoot was made on the fruiting (terminal) sections of shoots; this section typically averaging 12 cm in length and the average total shoot length is 33 cm in length.

Flowers are generally clustered and the width of the typical flower averages 7.6 mm, similar to 'Reka', and smaller than 'Nui' (averaging 10.3 mm). The color of the petals on fully open mature flowers is near White 155C.

Fruit

The fruit are small under New Zealand growing conditions, averaging approximately 1.1 g. Observations indicate fruit size to be smaller than that of fruit of the parent 'Reka' (2.1 g) and 'Nui' (3.2 g).

Generally, fruit is round to oblate in shape. Fruit diameter averages approximately 13 mm (observed range 11.9-14.6 mm) under New Zealand growing conditions. Unripe fruit is green, within the range near Yellow-Green 145B. Ripe fruit has an attractive bloom. Fruit color is light blue with the bloom intact, near Blue 103B, and skin color when bloom is completely removed is near Black 202A.

The pedicel scar is small to medium, approximately 1.8 mm in diameter, similar to 'Reka'. The scar is generally dry. The fruit sweetness is high and the Brix level averages 14.2%, (observed range 13.6-14.9%), higher than 'Reka' and 'Nui' (12% and 11.8% respectively).

The fruit acidity measured as titratable acidity (%) averaged 0.7, similar to 'Reka' and less than 'Nui' (0.8%). Fruit is generally firm, averaging 260 g/mm (observed range 250-290 g/mm), firmer compared with fruit of the varieties 'Reka' (averaged 168 g/mm) and 'Nui' (averaged 150 g/mm). Yield is high, over 4 Kg per adult plant, superior to 'Reka' and 'Island Blue'.

Seed size is approximately 1.6 mm with an average number of seeds per fruit of 22 (observed range approximately 10-33).

Events

According to observations under New Zealand growing conditions the time of vegetative bud burst was around the 20 August, about 20 days earlier than 'Reka'.

Time of beginning flowering recorded in New Zealand was around one week after the vegetative bud break, reaching an estimated 50% of flowering on 7 September, about 2 weeks after 'Island Blue' and around 3 weeks earlier than 'Nui' and 'Reka'.

The fruit maturity period occurs early in the season. In 2008 the stage where 50% of the fruit were mature was estimated at 28 November, about one week later than the plants of the parent 'Island Blue' and about 2 weeks earlier than 'Reka'.

Disease and Pests

The plant has shown symptoms of the early stage of rust infection (*Pucciniastrum vaccinii*) with little subsequent sporulation.

Geographical Adaptation

Observations indicate that the variety performs well in the cool temperate climate of the Waikato region, New Zealand, under standard management practices for commercial blueberry production. The plant cold hardiness according to the American zone classification has not been determined.

The invention claimed is:

1. A new and distinct Southern Highbush blueberry variety substantially as described in the specification and illustrations.

* * * * *